United States Patent
Sridhar et al.

(10) Patent No.: US 10,526,426 B2
(45) Date of Patent: Jan. 7, 2020

(54) PHOTOINITIATORS THAT ARE POLYMERIC OR POLYMERIZABLE FOR USE IN UV CURABLE PRESSURE SENSITIVE ADHESIVES

(71) Applicant: Henkel IP & Holding GmbH, Duesseldorf (DE)

(72) Inventors: Laxmisha Sridhar, Monmouth Junction, NJ (US); Eric N. Silverberg, Summit, NJ (US); Sean M. Burdzy, Hamden, CT (US); Andrew D. Messana, Newington, CT (US); John G. Woods, Farmington, CT (US); Bruce Stevens, Manville, NJ (US)

(73) Assignee: Henkel IP & Holding GmbH, Duesseldorf (DE)

( * ) Notice: Subject to any disclaimer, the term of this patent is extended or adjusted under 35 U.S.C. 154(b) by 123 days.

(21) Appl. No.: 15/702,199

(22) Filed: Sep. 12, 2017

(65) Prior Publication Data
US 2018/0016363 A1    Jan. 18, 2018

Related U.S. Application Data

(63) Continuation of application No. PCT/US2016/014662, filed on Jan. 25, 2016.
(Continued)

(51) Int. Cl.
*C08F 2/46* (2006.01)
*C09J 133/08* (2006.01)
(Continued)

(52) U.S. Cl.
CPC ............... *C08F 2/46* (2013.01); *C08F 2/48* (2013.01); *C08F 220/18* (2013.01);
(Continued)

(58) Field of Classification Search
CPC ...... C08F 2/46; C08F 283/065; C08F 283/02; C08F 2/48; C08F 220/18; C08F 2/50;
(Continued)

(56) References Cited

U.S. PATENT DOCUMENTS

| | | |
|---|---|---|
| 3,429,852 A | 2/1969 | Skoultchi |
| 7,745,505 B2 | 6/2010 | Liu et al. |

(Continued)

FOREIGN PATENT DOCUMENTS

| | | |
|---|---|---|
| CN | 1727320 A | 2/2006 |
| CN | 102304333 A | 1/2012 |

(Continued)

OTHER PUBLICATIONS

Lee et al., machine English translation of KR-10-2010-0116498 (Year: 2010).*

(Continued)

*Primary Examiner* — Jessica M Roswell
(74) *Attorney, Agent, or Firm* — James E. Piotrowski

(57) ABSTRACT

Disclosed are photoinitiators that are ultra violet (UV) reactive. The photoinitiators can be polymerized into polymeric backbones for use in UV curable hot melt pressure sensitive adhesives. The preferred polymeric backbones are acrylic-based polymers. The photoinitiators are very UVC sensitive and have excellent hot melt viscosity stability that is many fold higher than existing photoinitiators. The subject photoinitiators feature aryl ketones linked through an ether linkage to a variety of connector sequences that allow for polymerization of the photoinitiators.

8 Claims, 1 Drawing Sheet

Related U.S. Application Data

(60) Provisional application No. 62/135,867, filed on Mar. 20, 2015.

(51) Int. Cl.

| | | |
|---|---|---|
| *C08F 220/18* | (2006.01) | |
| *C08F 2/48* | (2006.01) | |
| *C08F 283/02* | (2006.01) | |
| *C09J 133/10* | (2006.01) | |
| *C08F 283/06* | (2006.01) | |
| *C08K 5/00* | (2006.01) | |
| *B32B 37/12* | (2006.01) | |

(52) U.S. Cl.
CPC ........ *C08F 283/02* (2013.01); *C08F 283/065* (2013.01); *C08K 5/0025* (2013.01); *C09J 133/08* (2013.01); *C09J 133/10* (2013.01); *B32B 2037/1215* (2013.01)

(58) Field of Classification Search
CPC . C09J 4/00; C09J 133/10; C09J 133/14; C09J 4/06; C09J 133/08; C08K 5/0025; C07C 323/12; C07C 69/54; B32B 2037/1215
See application file for complete search history.

(56) References Cited

U.S. PATENT DOCUMENTS

| | | |
|---|---|---|
| 7,799,884 B2 | 9/2010 | Herr et al. |
| 2011/0159203 A1 | 6/2011 | Loccufier et al. |
| 2012/0010317 A1 | 1/2012 | Schmitt et al. |
| 2013/0089581 A1 | 4/2013 | Nielsen et al. |
| 2013/0096220 A1 | 4/2013 | Nielsen et al. |
| 2014/0290856 A1 | 10/2014 | Hammond et al. |
| 2014/0303274 A1 | 10/2014 | Liu et al. |

FOREIGN PATENT DOCUMENTS

| | | | |
|---|---|---|---|
| CN | 102585045 A | 7/2012 | |
| CN | 102863323 A | 1/2013 | |
| CN | 103755842 A | 4/2014 | |
| KR | 2010116498 | * 11/2010 | ........... C07C 323/29 |
| WO | 9749664 A1 | 12/1997 | |
| WO | 2010028104 A1 | 3/2010 | |
| WO | 2010108752 A1 | 9/2010 | |

OTHER PUBLICATIONS

International Search Report for International PCT Patent Application No. PCT/US2016/014662 dated Jun. 2, 2016.

Czech et al., "Photoreactive UV-Crosslinkable Pressure-Sensitive Adhesives Based on Butyl Acrylate and 4-Acryloyloxy Benzophenone Copolymers", Journal of Research Updates in Polymer Science, 2012, vol. 1, No. 2, pp. 96-100.

Park et al., "Dual-Curable Acrylic Pressure-Sensitive Adhesives Based on UV and Thermal Processes", Macromolecular Research, 2008, vol. 16, No. 2, pp. 128-133.

Wang et al., "Novel one-component polymeric benzophenone photoinitiator containing poly (ethylene glycol) as hydrogen donor", Materials Chemistry and Physics, 2014, vol. 143, pp. 1391-1395.

Czech et al., "UV-inititated crosslinking of photoreactive acrylic pressure-sensitive adhesives using excimer laser", Polymer Bulletin, 2013, vol. 70, pp. 479-488.

Czech et al., "UV-crosslinkable acrylic pressure-sensitive adhesives for industrial application", Polymer Bulletin, 2012, vol. 69, pp. 71-80.

\* cited by examiner

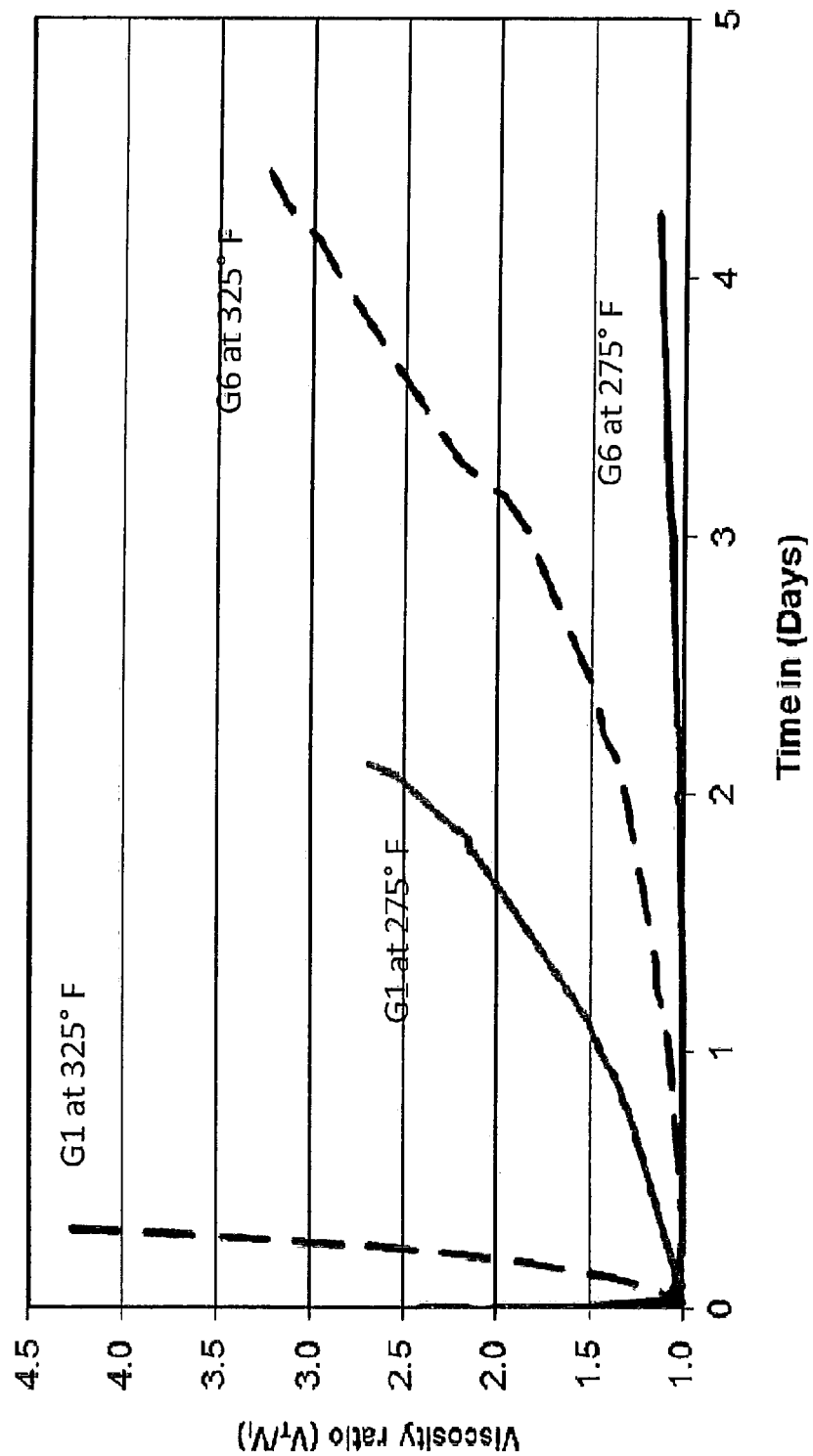

PHOTOINITIATORS THAT ARE POLYMERIC OR POLYMERIZABLE FOR USE IN UV CURABLE PRESSURE SENSITIVE ADHESIVES

This application is a continuation of International Application No. PCT/US2016/014662, filed Jan. 25, 2016, which claims the benefit of U.S. Provisional Patent Application No. 62/135,867 filed Mar. 20, 2015, the contents of each of which are incorporated herein by reference in their entirety.

TECHNICAL FIELD

This invention relates generally to pressure sensitive adhesives, and more specifically to photoinitiators that are polymerizable or polymeric for use in ultra violet curable hot melt pressure sensitive adhesives.

BACKGROUND OF THE INVENTION

Pressure sensitive adhesives that are ultra violet (UV) curable have been successfully used for label and tape applications for several years. Often the pressure sensitive adhesives (PSA) are polyacrylate based PSAs. Polyacrylates possess a variety of advantages over other adhesives because they are highly stable toward UV light, oxygen, and ozone which are found in abundance in the environment. Synthetic and natural rubber adhesives normally contain double bonds, which make these adhesives unstable to the aforementioned environmental effects. Further advantages of polyacrylates include their transparency and their serviceability within a relatively wide temperature range.

Polyacrylate PSAs are generally prepared in solvent solution by free radical polymerization of acrylic monomers and are then applied to a substrate from a solution using a coating bar. After application solvent is removed and they are dried on the substrate. Cohesive strength of an adhesive refers to the bond strength between the molecules of the adhesive while adhesive strength refers to the bond strength between the adhesive and a substrate. To increase its cohesive strength, the polymer is often crosslinked to a limited degree. Crosslinking or curing is done by exposure to either a thermal source or a UV source. This solvent process described is fairly costly and, as a general rule, the solvent is not recycled resulting in the high consumption of organic solvents and a high environmental burden. Moreover, it is very difficult to produce PSA tapes with a high adhesive application rate without also producing bubbles in the adhesive layer. One remedy is to use a hot melt process to apply the adhesive to a substrate. In this process, the PSA is applied to the backing material from the melt.

Hot melt pressure sensitive adhesives (HMPSAs) are thermoplastic compositions that combine the processing advantage of hot melt adhesives and the properties of pressure sensitive adhesives. Hot melt adhesives are solids at room temperature, melt at elevated temperatures, and enable easy coating on a substrate. Hot melt adhesives do not contain water or any solvents. They regain their solid form on cooling to form a permanently tacky solid coating on the substrate that adheres on contact to another substrate. These compositions are commonly applied to various substrates, such as paper, fabric, metal, and plastic films that are then converted into a large number of different products, especially pressure sensitive adhesive tapes and labels. These pressure sensitive adhesive products have a broad field of application in the automobile industry for fastening or sealing, in the pharmaceutical industry for bandages or transdermal drug delivery systems, and in the packaging industry for sealing, bonding or labeling.

Very low molecular weight polymers will yield hot melt pressure sensitive adhesives with sufficient fluidity, however the resulting adhesives lack cohesive strength. Very high molecular weight polymers give better cohesive strength, however these are often too viscous at the common application temperatures of from 175° F. to 356° F. to be easily coatable onto substrates. Achieving useable hot melt pressure sensitive adhesives requires balancing these two competing issues. To avoid the undesirable viscosity problems, polymers of moderate molecular weight have been made with various functional groups, photoinitiators, which undergo controlled crosslinking reactions upon exposure to UV radiation. In this manner, the cohesion of acrylic PSAs can be raised by providing sufficient crosslinking; however there still remain issues with hot melt viscosity and stability during application. The instability exhibits itself as a dramatic rise in viscosity of the HMPSA in the hot melt as it is heated. The viscosity instability can arise from incompatible functional groups on the polymer backbone or from unstable linkages such as urethane bonds in the polymer. The rapid increase in viscosity over a short period of time defeats the ability to apply the HMPSA to the substrate and thus the pot life of the typical HMPSA is very low.

It is desirable to create photoinitiators that can be polymerized into the polymer backbone in the HMPSA and that will provide sufficient crosslinking ability while maintaining the hot melt viscosity stability of the HMPSA at the typical usable temperatures.

SUMMARY OF THE INVENTION

In general terms, this invention provides acrylate polymers functionalized with UV curable photoinitiators that are very hot melt viscosity stable and that show good UV crosslinkability. In most cases the hot melt viscosity stability is on the order of 10 fold greater than prior art photoinitiators.

In one embodiment the present invention is a photoinitiator having a structure as defined in formula I below:

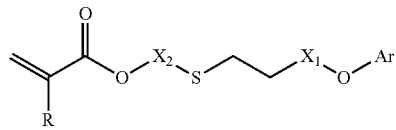

Formula I

Wherein: Ar is an aryl ketone moiety;

$X_1$ is optional, if present it is one of: $CH_2$; a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; or a cycloalkyl group containing at least one of heteroatoms, a carbonyl, an ester, a carbonate, and mixtures thereof at any position;

$X_2$ is one of: a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; or a cycloalkyl group containing at least one of heteroatoms, a carbonyl, an ester, a carbonate, and mixtures thereof at any position; and R is H or CH$_3$.

In one embodiment the present invention is a photoinitiator having a structure as defined in formula II below:

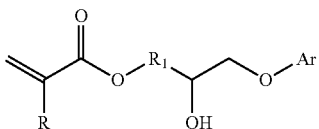

Formula II

Wherein: Ar is an aryl ketone moiety

R$_1$ is one of: a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; a cycloalkyl group containing at least one of heteroatoms, a carbonyl, an ester, a carbonate, and mixtures thereof at any position; a polyether; a polycaprolactone; or a polycarbonate; and R is H or CH$_3$.

In one embodiment the present invention is a photoinitiator having a structure as defined in formula III below:

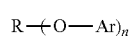

Formula III

Wherein: Ar is an aryl ketone moiety and n ranges from 1 to 10; and

R is a divalent or multivalent polymer backbone selected from the group consisting of: a linear, branched or hyper branched polyethylene glycol; a linear, branched or hyper branched polypropylene glycol; a linear, branched or hyper branched polytetrahydrofuran; a linear, branched or hyper branched polyester polyol; a linear, branched or hyper branched polycarbonate polyol; and a linear, branched or hyper branched polycaprolactone polyol.

In one embodiment the present invention is an ultra violet light curable polymer comprising: an acrylic polymer that is a reaction product of a plurality of one or more acrylic monomers and a plurality of one or more photoinitiators having a structure according to Formula I wherein said acrylic polymer is crosslinkable through said photoinitiator groups upon exposure to ultra violet light; and wherein said Formula I has the following structure

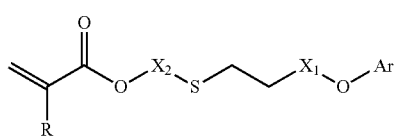

Formula I

Wherein: Ar is an aryl ketone moiety;

X$_1$ is optional, if present it is one of: CH$_2$; a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; or a cycloalkyl group containing at least one of heteroatoms, a carbonyl, an ester, a carbonate, and mixtures thereof at any position;

X$_2$ is one of: a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; or a cycloalkyl group containing at least one of heteroatoms, a carbonyl, an ester, a carbonate, and mixtures thereof at any position; and R is H or CH$_3$.

In one embodiment the present invention is an ultra violet light curable polymer comprising: an acrylic polymer that is a reaction product of a plurality of one or more acrylic monomers and a plurality of one or more photoinitiators having a structure according to Formula II wherein said acrylic polymer is crosslinkable through said photoinitiator groups upon exposure to ultra violet light; and wherein said Formula II has the following structure:

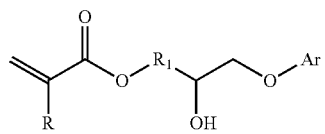

Formula II

Wherein: Ar is an aryl ketone moiety

R$_1$ is one of: a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; a cycloalkyl group containing at least one of heteroatoms, a carbonyl, an ester, a carbonate, and mixtures thereof at any position; a polyether; a polycaprolactone; or a polycarbonate; and R is H or CH$_3$.

In one embodiment the present invention is an ultra violet light curable polymer comprising: an acrylic polymer that is a reaction product of a plurality of one or more acrylic monomers and a plurality of one or more photoinitiators having a structure according to Formula III wherein said acrylic polymer is crosslinkable through said photoinitiator groups upon exposure to ultra violet light; and wherein said Formula III has the following structure

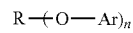

Formula III

Wherein: Ar is an aryl ketone moiety and n ranges from 1 to 10; and

R is a divalent or multivalent polymer backbone selected from the group consisting of: a linear, branched or hyper branched polyethylene glycol; a linear, branched or hyper branched polypropylene glycol; a linear, branched or hyper branched polytetrahydrofuran; a linear, branched or hyper branched polyester polyol; a linear, branched or hyper branched polycarbonate polyol; and a linear, branched or hyper branched polycaprolactone polyol.

In one embodiment the present invention is a hot melt pressure sensitive adhesive that is ultra violet light curable and comprises: an acrylic polymer that is a reaction product of a plurality of one or more acrylic monomers and a plurality of one or more photoinitiators having a structure according to Formula I, wherein said acrylic polymer is crosslinkable through said photoinitiator groups upon exposure to ultra violet light, and optionally a tackifier; and wherein said Formula I has the following structure

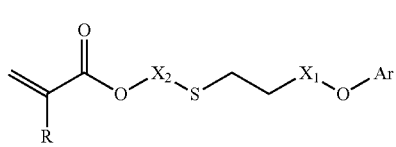

Formula I

Wherein: Ar is an aryl ketone moiety;
$X_1$ is optional, if present it is one of: $CH_2$; a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; or a cycloalkyl group containing at least one of heteroatoms, a carbonyl, an ester, a carbonate, and mixtures thereof at any position;
$X_2$ is one of: a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; or a cycloalkyl group containing at least one of heteroatoms, a carbonyl, an ester, a carbonate, and mixtures thereof at any position; and
R is H or $CH_3$.

In one embodiment the present invention is a hot melt pressure sensitive adhesive that is ultra violet light curable and comprises: an acrylic polymer that is a reaction product of a plurality of one or more acrylic monomers and a plurality of one or more photoinitiators having a structure according to Formula II, wherein said acrylic polymer is crosslinkable through said photoinitiator groups upon exposure to ultra violet light, and optionally a tackifier; and wherein said Formula II has the following structure

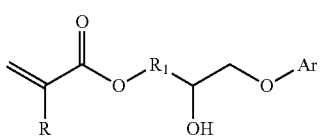

Formula II

Wherein: Ar is an aryl ketone moiety
$R_1$ is one of: a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; a cycloalkyl group containing at least one of heteroatoms, a carbonyl, an ester, a carbonate, and mixtures thereof at any position; a polyether; a polycaprolactone; or a polycarbonate; and
R is H or $CH_3$.

In one embodiment the present invention is a hot melt pressure sensitive adhesive that is ultra violet light curable and comprises: an acrylic polymer that is a reaction product of a plurality of one or more acrylic monomers and a plurality of one or more photoinitiators having a structure according to Formula III, wherein said acrylic polymer is crosslinkable through said photoinitiator groups upon exposure to ultra violet light, and optionally a tackifier; and wherein said Formula III has the following structure

Formula III

Wherein: Ar is an aryl ketone moiety and n ranges from 1 to 10; and
R is a divalent or multivalent polymer backbone selected from the group consisting of: a linear, branched or hyper branched polyethylene glycol; a linear, branched or hyper branched polypropylene glycol; a linear, branched or hyper branched polytetrahydrofuran; a linear, branched or hyper branched polyester polyol; a linear, branched or hyper branched polycarbonate polyol; and a linear, branched or hyper branched polycaprolactone polyol.

These and other features and advantages of this invention will become more apparent to those skilled in the art from the detailed description of a preferred embodiment. The drawings that accompany the detailed description are described below.

BRIEF DESCRIPTION OF THE DRAWINGS

FIG. 1 shows the hot melt viscosity over time of an acrylic polymer containing a control photoinitiator not in accordance with the present invention and the same polymer containing a photoinitiator in accordance with the present invention, each at two different temperatures.

DETAILED DESCRIPTION OF A PREFERRED EMBODIMENT

In the present specification and claims the following abbreviations apply. Hot melt pressure sensitive adhesive (HMPSA); pressure sensitive adhesive (PSA); grams (g); milligrams (mg); parts per million (ppm); millimoles (mmol); liter (L); milliliter (ml); Fahrenheit (F); Celsius (C); ultra violet (UV); ultra violet C (UVC); aryl ketone moiety (Ar); and the term acrylic polymer is meant to refer in general to polymers or copolymers formed from reaction of acrylic-based monomers unless otherwise noted.

"Alkyl" or "alkane" refers to a hydrocarbon chain or group containing only single bonds between the chain carbon atoms. The alkane can be a straight hydrocarbon chain or a branched hydrocarbon group. The alkane can be cyclic. The alkane can contain 1 to 20 carbon atoms, advantageously 1 to 10 carbon atoms and more advantageously 1 to 6 carbon atoms. In some embodiments the alkane can be substituted. Exemplary alkanes include methyl, ethyl, n-propyl, isopropyl, isobutyl, n-butyl, sec-butyl, tert-butyl, isopentyl, neopentyl, tert-pentyl, isohexyl and decyl.

"Alkenyl" or "alkene" refers to a hydrocarbon chain or group containing one or more double bonds between the chain carbon atoms. The alkenyl can be a straight hydrocarbon chain or a branched hydrocarbon group. The alkene can be cyclic. The alkene can contain 1 to 20 carbon atoms, advantageously 1 to 10 carbon atoms and more advantageously 1 to 6 carbon atoms. The alkene can be an allyl group. The alkene can contain one or more double bonds that are conjugated. In some embodiments the alkene can be substituted.

"Alkoxy" refers to the structure —OR, wherein R is hydrocarbyl.

"Alkyne" or "alkynyl" refers to a hydrocarbon chain or group containing one or more triple bonds between the chain carbon atoms. The alkyne can be a straight hydrocarbon chain or a branched hydrocarbon group. The alkyne can be cyclic. The alkyne can contain 1 to 20 carbon atoms, advantageously 1 to 10 carbon atoms and more advantageously 1 to 6 carbon atoms. The alkyne can contain one or more triple bonds that are conjugated. In some embodiments the alkyne can be substituted.

"Aryl" or "Ar" refers to a monocyclic or multicyclic aromatic group. The cyclic rings can be linked by a bond or fused. The aryl can contain from 6 to about 30 carbon atoms; advantageously 6 to 12 carbon atoms and in some embodiments 6 carbon atoms. Exemplary aryls include phenyl, biphenyl and naphthyl. In some embodiments the aryl is substituted.

"Ester" refers to the structure R—C(O)—O—R' where R and R' are independently selected hydrocarbyl groups with or without heteroatoms. The hydrocarbyl groups can be substituted or unsubstituted.

"Halogen" or "halide" refers to an atom selected from fluorine, chlorine, bromine and iodine.

"Hetero" refers to one or more heteroatoms in a structure. Exemplary heteroatoms are independently selected from N, O and S.

"Heteroaryl" refers to a monocyclic or multicyclic aromatic ring system wherein one or more ring atoms in the structure are heteroatoms. Exemplary heteroatoms are independently selected from N, O and S. The cyclic rings can be linked by a bond or fused. The heteroaryl can contain from 5 to about 30 carbon atoms; advantageously 5 to 12 carbon atoms and in some embodiments 5 to 6 carbon atoms. Exemplary heteroaryls include furyl, imidazolyl, pyrimidinyl, tetrazolyl, thienyl, pyridyl, pyrrolyl, thiazolyl, isothiazolyl, oxazolyl, isoxazolyl, thiazolyl, quinolinyl and isoquinolinyl. In some embodiments the heteroaryl is substituted.

"Hydrocarbyl" refers to a group containing carbon and hydrogen atoms. The hydrocarbyl can be linear, branched, or cyclic group. The hydrocarbyl can be alkyl, alkenyl, alkynyl or aryl. In some embodiments, the hydrocarbyl is substituted.

"(Meth)acrylate" refers to acrylate and methacrylate.

"Polyether" refers to polymers which contain multiple ether groups (each ether group comprising an oxygen atom connected to two hydrocarbyl groups) in the main polymer chain. The repeating unit in the polyether chain can be the same or different. Exemplary polyethers include homopolymers such as polyoxymethylene, polyethylene oxide, polypropylene oxide, polybutylene oxide, polytetrahydrofuran, and copolymers such as poly(ethylene oxide co propylene oxide), and EO tipped polypropylene oxide.

"Polyester" refers to polymers which contain multiple ester linkages. A polyester can be either linear or branched.

"Polymer" refers to any polymerized product greater in chain length and molecular weight than the oligomer. Polymers can have a degree of polymerization of about 20 to about 25000. As used herein polymer includes oligomers and polymers.

"Substituted" refers to the presence of one or more substituents on a molecule in any possible position. Useful substituents are those groups that do not significantly diminish the disclosed reaction schemes. Exemplary substituents include, for example, H, halogen, (meth)acrylate, epoxy, oxetane, urea, urethane, $N_3$, NCS, CN, NCO, $NO_2$, $NX^1X^2$, $OX^1$, $C(X^1)_3$, $C(halogen)_3$, $COOX^1$, $SX^1$, $Si(OX^1)_iX^2_{3-i}$, alkyl, alkoxy; wherein $X^1$ and $X^2$ each independently comprise H, alkyl, alkenyl, alkynyl or aryl and I is an integer from 0 to 3.

The present invention is directed toward creation of polymerized or polymerizable photoinitiators for use in UV curable pressure sensitive adhesives (PSAs), and more specifically for hot melt pressure sensitive adhesives (HMPSAs). The present invention addresses these issues by providing acrylate polymers functionalized with pendant UV photoinitiators that are hot melt stable and that show good UV crosslinkability. The polyacrylates useful in the present invention comprise a wide range of acrylic polymers. Preferably the acrylic polymers suitable for use in the present invention have a weight average molecular weight in the range of from 10,000 to 1,000,000, more preferably from 50,000 to 600,000 as measured by gel permeation chromatography or by relative viscosity. The polyacrylates can be formed from any acrylic monomers including, by way of example only, acrylic acid, methacrylates, methyl methacrylates, ethyl acrylates, 2-chloroethyl vinyl ethers, 2 ethylhexyl acrylate, acetoacetoxyethyl methacrylate (AAEM), hydroxyethyl methacrylate, butyl acrylate, butyl methacrylate, trimethylolpropane triacrylate (TMPTA).

In one embodiment, the present inventive photoinitiators have the structure according to formula I or formula II. These photoinitiators can be polymerized into a polymeric backbone of a polyacrylate as described herein and then subsequently crosslink to other polyacrylate backbones. In another embodiment the photoinitiators have the structure according to formula III, these all include a polymeric backbone in their own right. Preferably the photoinitiators according to formula III are further combined with a polyacrylate and can crosslink with the polyacrylate also. The various embodiments of the inventive photoinitiators are fully described below.

In one embodiment the photoinitiators according to the present invention have the following structural formula (Formula I):

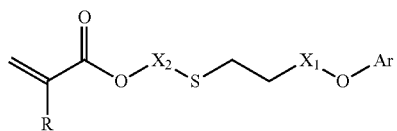

Formula I

Wherein:

Ar is an aryl ketone moiety;

$X_1$ is optional, if present it is one of: $CH_2$; a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; or a cycloalkyl group containing at least one of heteroatoms, a carbonyl, an ester, a carbonate, and mixtures thereof at any position;

$X_2$ is one of: a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; or a cycloalkyl group containing at least one of heteroatoms, a carbonyl, an ester, a carbonate, and mixtures thereof at any position; and R is H or $CH_3$.

When $X_1$ is not present in the above Formula I, the Ar is bonded to the oxygen which is in turn bonded to the thiol through a linkage of —$CH_2$—$CH_2$—. Particularly preferred aryl ketone moieties include ones wherein Ar is selected from the group consisting of:

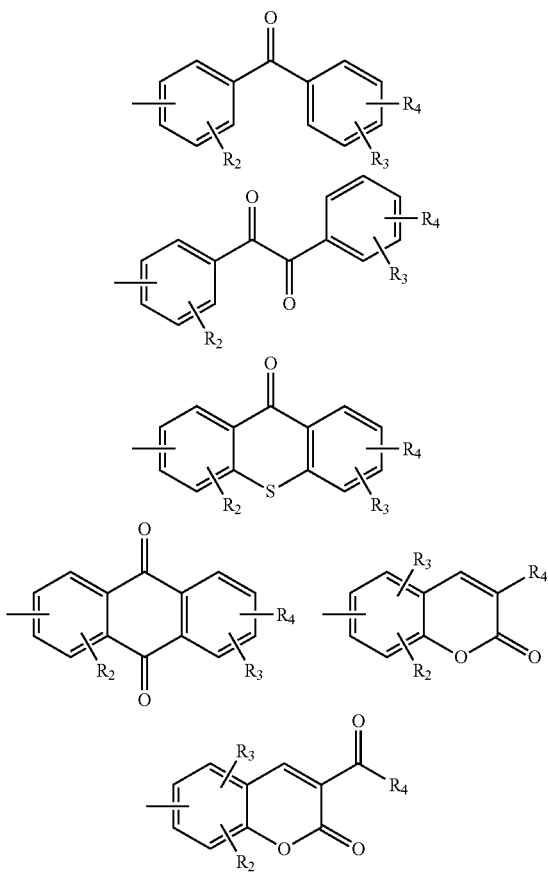

Wherein:

$R_2$, $R_3$ and $R_4$ are independently: a linear alkyl group; a branched alkyl group; a cycloalkyl group; an alkylenoxy group; an alkenyl group; an aryl group; or an alkyl group containing a heteroatom; a carbonyl group; H; F; Cl; Br; I; OR; $NR_2$; or SR wherein R in OR, $NR_2$, or SR is one of an alkyl, an aryl, or a heteroaryl group.

The above sulfide containing aryl ketone acrylates and methacrylates according to Formula I can be obtained by the thiol-ene click reaction of hydroxy functional thiols with 4-alkenyloxyaryl ketones, followed by acrylation of the hydroxyl group. These 4-alkenyloxyaryl ketones can in turn be obtained by alkylation or vinylation of 4-hydroxyaryl ketones. Several examples of alkylating agents that can be used include, but are not limited to, allyl bromide (chloride), crotyl bromide(chloride), 4-bromo(chloro)-1-butene, 5-bromo(chloro)-1-pentene, 6-bromo(chloro)-1-hexene, 7-bromo(chloro)-1-heptene, 8-bromo(chloro)-1-octene, 9-bromo(chloro)-1-nonene. These alkene functional halides are available commercially.

The hydroxyl functional thiols used for the thiol-ene click reaction in this invention are varied and can include, by way of example and not limitation, linear or branched thiols and they can contain aliphatic, aromatic, or alicyclic backbones optionally interrupted by hetero atoms, or can contain one or more of carbonyl, ester or carbonate linkages. Some non-limiting examples of suitable hydroxyl functional thiols that can be used include: 2-mercpato-1-ethanol, 3-mercapto-1-propanol, 1-mercapto-2-propanol, 4-mercapto-1-butanol, 6-mercapto-1-hexanol, 8-mercapto-1-octanol, 11-mercapto-1-undecanol, 9-mercapto-1-nonanol, (11-Mercaptoundecyl) hexa(ethylene glycol), (11-Mercaptoundecyl) tetra(ethylene glycol), hydroxyalkyl esters of thioglycolic acid and 3-mercaptopropionic acid. Other examples of hetero atom containing hydroxyl functional thiols include polyethylene glycol (PEG) based ones having HS-PEG-OH structures like PBL-8080, 8081, 8082, 8083, 8084, which are available from Creative PEG works. These range in size from a molecular weight of 1000 to 10,000.

In another embodiment of the present invention the photoinitiators have the following structural formula (Formula II):

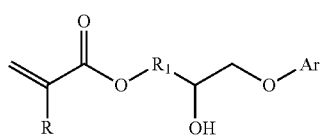

Formula II

Wherein:

Ar is an aryl ketone moiety;

$R_1$ is one of: a linear alkyl group; a branched alkyl group; a cycloalkyl group; a linear alkyl group containing at least one of heteroatoms, a carbonyl, an ester, a carbonate, and mixtures thereof in any position; a branched alkyl group containing at least one of heteroatoms, a carbonyl, an ester, a carbonate, and mixtures thereof at any position; a cycloalkyl group containing at least one of heteroatoms, a carbonyl, an ester, a carbonate, and mixtures thereof at any position; a polyether; a polycaprolactone; or a polycarbonate; and R is H or $CH_3$.

These hydroxyl functional aryl ketone acrylates and methacrylates according to Formula II can be obtained by the reaction of 4-hydroxyaryl ketones with glycidyl functional acrylates or methacrylates under catalysis. Some nonlimiting examples of glycidyl functional acrylates and methacrylates that can be used for reaction with 4-hydroxy aryl ketones include, by way of example and not limitation, glycidyl acrylate, glycidyl methacrylate, and 4-hydroxybutyl acrylate glycidyl ether, which are available commercially.

In another embodiment of the present invention the photoinitiators according to the present invention have the following structural formula (Formula III):

Formula III

Wherein:

Ar is an aryl ketone moiety and n ranges from 1 to 10; and R is a divalent or multivalent polymer backbone selected from the group consisting of: a linear, branched or hyper branched polyethylene glycol; a linear, branched, or hyper branched polypropylene glycol; a linear, branched or hyper branched polytetrahydrofuran; a linear, branched or hyper branched polyester polyol; a linear, branched or hyper branched polycarbonate polyol; and a linear, branched or hyper branched polycaprolactone polyol. The Ar groups in Formula III can be pendant, terminal, or a mixture thereof. The formed HMPSA using Formula III can be star type core polymers after the combination of an acrylic polymer and the polymer photoinitiator according to formula III.

Another embodiment of the present invention is directed to UV curable acrylic polymers comprising the photoinitiators described above, wherein the photoinitiator is polymerized into the acrylic polymer backbone by a covalent linkage when the photoinitiator is according to Formula I or II prior to UVC cured crosslinking. For the Formula III photoinitiator the acrylic polymer is combined with the photoinitiator polymer and then the mixture is cured by UVC and the photoinitiator crosslinks the acrylic polymer chains by an H abstraction and radical recombination reaction. Yet another aspect of the present invention is directed to UV crosslinkable hot melt pressure sensitive adhesives comprising the acrylic polymers having the photoinitiators described above. Preferably the photoinitiators according to the present invention are used in an amount of from 0.1 to 10 mole % in the acrylic polymers, more preferably from 0.2 to 5.0 mole % based on the total number of moles of acrylate monomers used for polymerization to obtain the acrylate polymer. The adhesive according to the present invention may be used in the manufacture of articles as described above such as, for example, industrial and medical tapes and articles of manufacture comprising the adhesives. The present inventive HMPSA compositions can be applied to various substrates, such as, by way of example only, paper, fabric, metal, plastic films, foams, foils, glass, natural rubber, synthetic rubber, wood, plywood and other substrates. The substrates can then be converted into a large number of different products and articles, especially pressure sensitive adhesive tapes and labels. Preferably, the present inventive hot melt pressure sensitive adhesives are applied to substrates at levels of from 20 to 150 grams/meter$^2$. These pressure sensitive adhesive products have a broad field of application. In the automobile industry they are for fastening or sealing, for example. In the medical and pharmaceutical industry they are used, for example, in bandages, gauze wraps, surgical tapes, and transdermal drug delivery systems. In the packaging and mailing industry they are used for sealing, bonding, and labeling, for example.

The HMPSA is typically a solid at room temperature. It is heated to a molten or fluid state prior to use. The molten HMPSA can be applied to the substrate by any manner including by roller, slot orifice, spray or extrusion coating. The curing of the HMPSAs of the present invention is preferably accomplished using UVC radiation, the amount required to transform the composition into an elastomeric adhesive of high cohesion and high adhesion is dependent on the intensity of the radiation, the amount of the photoinitiator, the thickness of the adhesive layer, the distance between the radiation source and the adhesive film, and environmental factors. Any source of UVC radiation is suitable.

Generally speaking the PSAs and HMPSAs include in the formulation one or more tackifiers to increase their bonding characteristics to low energy surfaces such polyethylene or polypropylene surfaces. The most commonly used tackifiers in acrylic pressure sensitive adhesives include rosin esters, terpene phenols, esters of hydrogenated rosins, synthetic hydrocarbons and combinations thereof. Preferred tackifiers are esters of hydrogenated rosins as they exhibit high levels of tack, oxidation resistance, and limited interference with UV radiation used in post polymerization crosslinking. By way of example and not limitation, three examples of suitable tackifiers are Foral® 85 and Foral® 105, available from Pinova® and Pensel GA-100, available from Arakawa. The Foral® 85 tackifier is described by Pinova® as a thermoplastic resin that is a glycerol ester of highly hydrogenated refined wood resin. The Foral® 105 tackifier is described by Pinova® as a thermoplastic resin that is a pentaerythritol ester of highly hydrogenated refined wood resin. The Pensel GA-100 is described by Arakawa as a pentaerythritol ester of Rosin esters.

Tackifiers are typically added at levels from 5-50 parts per 100 parts dry polymer with a preferred range of 10-40 parts per 100 parts dry polymer. The solvent in the polymer is stripped off prior to combination of the tackifier with the polymer photoinitiator combination. It should be noted that the addition of tackifiers can have undesirable effects such as raising the glass transition temperature ($T_g$) of the system and reducing the cohesive strength. The tackifiers listed above are quite useful for tackifying the acrylic copolymers of this invention. The particular tackifying resin and/or the amounts used will depend upon the acrylic copolymer.

The PSAs and HMPSAs can optionally include in their formulations one or more additives and combinations of additives. The additives include, by way of example: photosynergists, ultraviolet absorbers, hindered amine light stabilizers, adhesion promoters, fillers, tackifiers, plasticizers, flow aids, wetting aids, rheology modifiers, dyes, pigments, nucleating agents, antioxidants, and combinations thereof. The additives may be used a widely variable levels ranging, per additive, at from 0.05 to 100% by weight based on the total dried polymer weight.

Synthesis of Photoinitiators According to the Present Invention

In a first series will be described several processes for the synthesis of a photoinitiator according to Formula I of the present invention, this initiator will be designated G6 in the present specification and claims. Methods for the preparation of G6 and its methacrylate version are described below. The photoinitiator G6 has the following structure, as confirmed by both proton nuclear magnetic resonance ($^1$H NMR) and liquid chromatography-mass spectrometry (LC-MS) analysis:

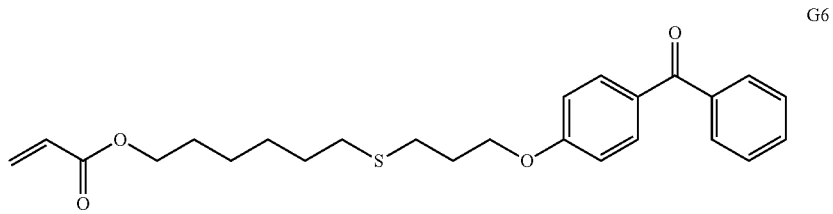 [SMILES: C=CC(=O)OCCCCCCSCCCOc1ccc(C(=O)c2ccccc2)cc1]

G6

The following components were added to a 2 L 4 necked flask equipped with a mechanical stirrer, nitrogen inlet and reflux condenser: 230.7 g (968 mmol) of 4-allyloxybenzophenone and 136.5 g (1016 mmol) of 6-mercaptohexanol in 420 ml of toluene. Nitrogen was bubbled through the solution for 45 minutes as the mixture warmed to 60° C. Then 1.59 g (9.68 mmol) of azobisisobutyronitrile (AIBN) was added and nitrogen was further bubbled for about 15 minutes. The bubbling was stopped and the mixture stirred at 80° C. under a nitrogen atmosphere for about 2 hours and then refluxed for another 2 hours under nitrogen. Then 367 mg (1000 ppm) of methylhydroquinone was added and the mixture further refluxed for 30 minutes. After cooling, an additional 420 ml of toluene was added and the mixture was further cooled to 0 to 5° C. with an ice-water mixture bath under nitrogen. Once the temperature was reduced to about 5° C., 127.4 g (1258 mmol) of triethylamine and a catalytic amount, 200 mg, of 4-dimethylaminopyridine (DMAP) were added. Then 105.2 g (1162 mmol) of acryloyl chloride was added in lots using a syringe to keep the temperature of the mixture in the range of from 5 to 18° C. After the final addition of acryloyl chloride, the mixture was slowly warmed to room temperature and stirred overnight. Then 500 ml of a 1:1 ethyl acetate:heptane solution was added, briefly stirred and allowed to stand. The precipitate was filtered off using suction filtration and the filter cake washed with another 250 ml of 1:1 ethyl acetate:heptane. Then 500 ppm of methylhydroquinone was added to the organic layer and the solvent evaporated using a rotovap to give the photoinitiator G6 as a yellow liquid, 352 g, a yield of 85%.

In an alternative method for synthesis of the photoinitiator G6 one can utilize a transesterification reaction of the intermediate thiol-ene adduct from above, which is the product prior to addition of the trimethylamine and DMAP. To a 100 ml round bottom flask equipped with an external heating, magnetic stirring, thermo-probe, nitrogen inlet, condenser with a Dean-Stark trap the following were added: 5 g (13 mmol) of intermediate thiol-ene adduct, prepared as described above, and 30 ml of heptane. Then 4.03 g (39.87 mmol) of ethyl acrylate in 30 ml of heptane was added and the mixture warmed with stirring. Once the reaction temperature was near 60° C. 0.29 g (0.1 mmol) of tetraisopropyl titanate catalyst was added. A cloudy mixture thus obtained was heated with stirring to distillation under a nitrogen atmosphere. The flask vapor tube was wrapped with cotton to facilitate distillation. Distillation began near 92° C., pot temperature, and gradually the temperature increased to about 97.1° C. in about 4 hours. The heating was continued for another hour for a total of 5 hours to a temperature of 98.3° C. The transesterification reaction was ended and the reaction flask cooled to 10° C. resulting in a pale yellow oil collected near the bottom. The clear liquid was decanted and the pale yellow oil was washed twice with heptane, 20 ml per wash each, with stirring for 10 minutes each time. The pale oil was redissolved in 20 ml of ethyl acetate and the resulting clear liquid was washed twice with water, 10 ml each wash. The organic layer was separated and dried over anhydrous $Na_2SO_4$ for approximately 30 minutes. The dried liquid was gravity filtered through Whatman filter paper to provide a colorless liquid and then the solvent was evaporated in a rotovap to give photoinitiator G6.

In another synthesis method the photoinitiator G6 methacrylate was formed as described below, the structure was confirmed by $^1H$ NMR and LC-MS analysis.

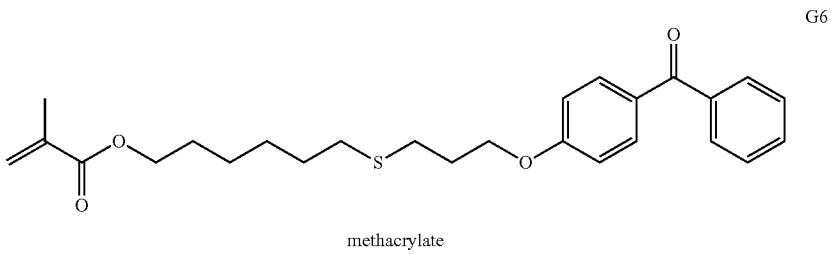 [SMILES: C=C(C)C(=O)OCCCCCCSCCCOc1ccc(C(=O)c2ccccc2)cc1]

G6 methacrylate

The following were added to a 2 L 4 necked flask equipped with a mechanical stirrer, nitrogen inlet and reflux condenser: 140 g (587 mmol) of 4-allyloxy benzophenone and 82.8 g (616 mmol) of 6-mercaptohexanol in 250 ml of toluene. Nitrogen was bubbled through the solution for 45 minutes as the mixture warmed to 60° C. Then 964 mg (5.87 mmol) of AIBN was added and the nitrogen further bubbled for about 15 minutes. The bubbling was stopped and the mixture stirred at 80° C. under a nitrogen atmosphere for about 2 hours and then refluxed for 2 hours under nitrogen. Then 367 mg (1000 ppm) of methylhydroquinone was added and the mixture further refluxed for 30 minutes. After cooling, another 100 ml of toluene and 5.6 g (29 mmol) of p-toluenesulfonic acid (PTSA) were added and the mixture refluxed with azeotropic removal of water for about 4 hours. After cooling to room temperature about 220 ml of aq. saturated $NaHCO_3$ solution, made by combining 20 g of $NaHCO_3$ with 200 ml of water, was added slowly and stirred for 30 minutes. Then 400 ml of ethyl acetate was added and stirred. After allowing the layers to separate, the organic layer was dried over anhydrous Na$_2$SO$_4$ for approximately 30 minutes. Then another 100 mg of methylhydroquinone was added and the solvent was evaporated to give the methacrylated G6 photoinitiator as an orange liquid, 233 g, a yield of 89%.

Another photoinitiator in accordance with the present invention was synthesized as described below. This photoinitiator is an example according to Formula II described above and is designated as G10 in the present specification and claims. The structure was confirmed by $^1$H NMR and LC-MS analysis.

G10

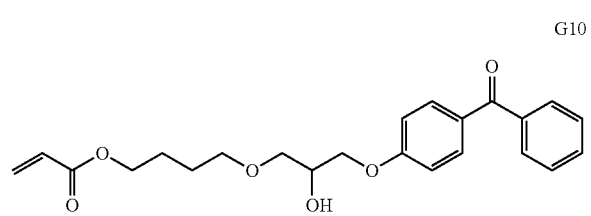 [SMILES: C=CC(=O)OCCCCOCC(O)COc1ccc(C(=O)c2ccccc2)cc1]

The following components were added to a 250 ml 3 necked flask equipped with a magnetic stirrer and nitrogen inlet: 18.9 g (95 mmol) of 4-hydroxybenzophenone and a catalytic amount, 0.37 g (6 mmol), of KOH. The mixture was flushed with nitrogen for 5 minutes. Then 18.52 g (92 mmol) of 4-hydroxybutyl acrylate glycidyl ether and 2000 ppm of methylhydroquinone were added and the mixture was heated to 80° C. The mixture became an orange homogenous liquid when the temperature reached about 70° C. The reaction was further stirred at 80° C. for about 9 hours. Then after cooling to room temperature, 200 ml of ethyl acetate was added and the organic layer washed with 70 ml of 10% aqueous KOH solution once followed by two washes with water. The solvent was evaporated using a rotovap to give the hydroxyl functional benzophenone acrylate G10 as a viscous grange liquid, 33 g, a yield of 88%.

In a next series two examples of photoinitiators in accordance with Formula III of the present invention were created as described below. The first was a polypropylene glycol (PPG) benzophenone derivative designated as G11, the structure was confirmed by $^1$H NMR analysis.

G11

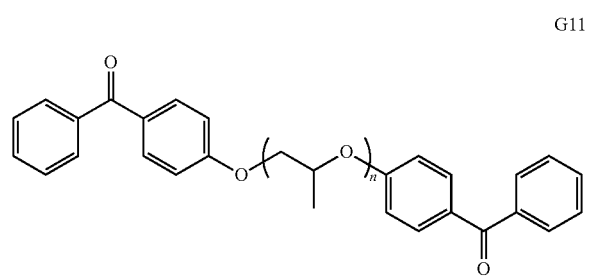

The following components were added to a 1 L 4 necked flask equipped with a mechanical stirrer and nitrogen inlet: 50 g of 425 Mn polypropylene glycol (118 mmol) in 500 ml of CH$_2$Cl$_2$. The mixture was cooled to 0 to 5° C. with a bath of an ice-water mixture under a nitrogen atmosphere. Then 29.99 g (356 mmol) of triethylamine was added and stirred for 15 minutes. A solution of methanesulfonyl chloride, 31 g (308 mmol) in 50 ml of CH$_2$Cl$_2$, was added slowly drop wise over a period of 30 minutes. The mixture was slowly warmed to room temperature and stirred for 4 hours. The CH$_2$Cl$_2$ was evaporated using a rotovap. Then 500 ml of ethyl acetate was added and the solution was washed several times with water and then dried over anhydrous Na$_2$SO$_4$ for approximately 30 minutes. The solvent was evaporated to give the corresponding PPG mesylate as a yellow oil, 63 g, for a yield of 93%. The structure as confirmed by $^1$H NMR analysis.

The following were added to a 250 mL flask equipped with a magnetic stirrer and nitrogen inlet: 35.86 g (181 mmol) of 4-hydroxybenzophenone in 250 ml of dimethyl sulfoxide (DMSO). A 50% methanolic solution of KOH, 10.15 g (181 mmol) was added to the flask and the mixture warmed to 80° C. Then 49.89 g (86.2 mmol) of the PPG mesylate in 75 ml of DMSO was added at once and the reaction stirred at 100° C. overnight. After cooling to room temperature, 150 ml of a 10% aqueous KOH solution was added and stirred for 15 minutes. The product was extracted with 500 ml of ethyl acetate. The organic layer was washed once more with 100 ml of a 10% aqueous KOH solution, washed with water, and then dried over anhydrous Na$_2$SO$_4$ for approximately 30 minutes. Solvent evaporation gave the PPG benzophenone derivative as a brown oil, 51 g, for a yield of 86%.

The second photoinitiator in accordance with Formula III was a polyethylene glycol benzophenone derivative designated as G12 as shown below. It was synthesized as described below and the structures of the intermediate and final product were confirmed by $^1$H NMR analysis.

G12

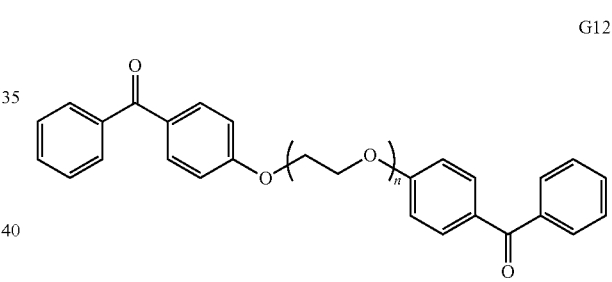

The following were added to a 500 ml 4 necked flask equipped with a nitrogen inlet and magnetic stir bar: 35 g of 400 Mn polyethylene glycol (87.5 mmol) in 300 ml of CH$_2$Cl$_2$. The mixture was cooled to 0 to 5° C. with an ice-water mixture bath. After stirring for 15 minutes, 22.14 g of triethylamine (218 mmol) was added. Then 23.05 g (201 mmol) of methanesulfonyl chloride was added drop wise over a period of 30 minutes. The mixture was slowly warmed to room temperature and further stirred overnight. The CH$_2$Cl$_2$ was evaporated and 300 ml of 2:1 ethyl acetate: heptane mixture was added. The salts were gravity filtered off using Whatman filter paper and then it was washed with another 100 ml of 2:1 ethyl acetate:heptane mixture. The solvent was evaporated using a rotovap to give the intermediate PEG mesylate, 39 g, a yield of 80%.

The following were added to a 500 ml flask equipped with a magnetic stir bar: 26.8 g (135 mmol) of 4-hydroxybenzophenone in 250 ml of DMSO. To this was added 7.64 g (136 mmol) of a 50% methanolic solution of KOH. The mixture was stirred at 80° C. for about 30 minutes. Then 35.6 g (64 mmol) of the PEG mesylate in 50 ml of DMSO was added at once and the mixture stirred at 100° C. for 24 hours. After cooling to room temperature 100 ml of a 10% aqueous KOH solution was added and stirred for 15 minutes. The product was extracted with 200 ml of ethyl acetate twice. The organic layer was washed with 100 ml of a 10% aqueous KOH solution, and then twice with water. After drying over anhydrous $Na_2SO_4$, the solvent was evaporated to give the PEG benzophenone G12 as a brown oil, 43 g, for a yield of 84%.

Photoinitiators according to Formula III as illustrated in G11 and G12 preferably include 1 to 300 polymerizable units, meaning in the formulas for G11 and G12 n is equal to 1 to 300.

Synthesis of the control, not in accordance with the present invention photoinitiator G1 has been described in U.S. Pat. No. 7,745,505, the description of which is incorporated by reference.

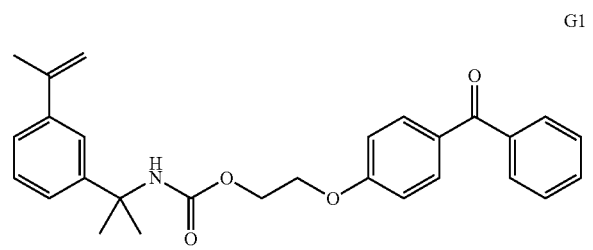 [SMILES: C=C(C)c1cccc(C(C)(C)NC(=O)OCCOc2ccc(C(=O)c3ccccc3)cc2)c1]

G1

Synthesis of Polymers Containing the Photoinitiators According to the Present Invention An acrylic polymer incorporating the photoinitiator G6 in accordance with the present invention was prepared as follows. A monomer mix containing 2-ethylhexyl acrylate, butyl acrylate, methyl acrylate, acrylic acid, photoinitiator G-6, ethyl acetate as a solvent, and 2,2'-azobisisobutyronitrile (AIBN) as the polymerization initiator was prepared. A fraction was charged to an appropriate vessel and heated to reflux with stirring. The remainder was added to the vessel over time. The weight ratios of the monomers and initiator added in totality were the following: 2-ethylhexyl acrylate: butyl acrylate:methyl acrylate:acrylic acid:photoinitiator: AIBN were 17.7:55:25.5:1:0.52:0.33. The material was then held at reflux for a suitable period of time as known to those of skill in the art. At the end of the hold period, a second initiator, tertiary amyl peroxypivalate, was added in the weight ratio of 0.23 and the batch held at reflux to scavenge the remaining monomers. The contents were cooled to room temperature. The resulting polymer was 50% solids and had a Brookfield viscosity of 2775 centipoise (cP), spindle #2 at 20 revolutions per minute (rpm). The relative viscosity of the resultant polymer was 2.62, using a 2.2% ethyl acetate reference solution. As known by those of skill in the art formation of acrylic polymers useful in the present invention can proceed by solution, emulsion, or bulk polymerization procedures using well known polymerization techniques such as free radical polymerization, anionic polymerization, and cationic polymerization techniques. The acrylic monomers used can comprise by way of example: acrylic acid, methacrylates, methyl methacrylates, ethyl acrylates, 2-chloroethyl vinyl ethers, 2 ethylhexyl acrylate, acetoacetoxyethyl methacrylate (AAEM), hydroxyethyl methacrylate, butyl acrylate, butyl methacrylate, trimethylolpropane triacrylate (TMPTA), and mixtures thereof. The ratios of the monomers can be varied within wide ranges to form acrylic polymers useful in the present invention. Preferably the acrylic polymers used in the present invention have weight average molecular weights of from 10,0000 to 1,000,000 and more preferably from 50,000 to 600,000.

A similar recipe was used for the synthesis of acrylic polymer with photoinitiator G-10 according to the present invention. The resulting polymer was 51.25% solids and had a Brookfield viscosity of 2,575 centipoise (cP), spindle #2 at 20 revolutions per minute (rpm). The relative viscosity of the resultant polymer was 2.5, using a 2.2% ethyl acetate reference solution.

An acrylic polymer containing the control, not according to the present invention, photoinitiator G1 was prepared as described above for formation of the polymer containing G6 except that the G1 was directly substituted for the G6. The resulting polymer was 51.12% solids and had a Brookfield viscosity of 2,150 centipoise (cP), spindle #2 at 20 revolutions per minute (rpm). The relative viscosity of the resultant polymer was 2.44, using a 2.2% ethyl acetate reference solution.

Acrylic polymers with the selected photoinitiators were prepared by combining the acrylic polymer plus photoinitiator with the tackifier Foral® 105 at a ratio of 20 parts tackifier per 100 parts dry polymer. This was done with the polymers containing G6 and G1.

Experimental Data

Hot Melt Viscosity Stability

The hot melt viscosity stability of the acrylic polymer containing G1, control not according to the present invention, was compared to the acrylic polymer containing G6 at two temperatures. The temperatures chosen were 275° F. (135° C.) and 325° F. (162.7° C.). The viscosity was tested using 10.5 grams of each adhesive sample in a Brookfield Thermocel hotmelt viscometer. The viscosity was tested every 30 minutes until a viscosity minimum had been determined. Thereafter the viscosity was measured every hour until the test was terminated. The data is normalized to the initial viscosity at time 0. The results are shown in FIG. 1 which presents normalized viscosity versus time in days. The dotted lines are the data for the polymers containing G1, the control, or G6, according to the present invention, at 325° C. The solid lines are the data for the polymer containing G1 or G6 at 275° C. As the testing temperature is increased the viscosity changes are more rapid. Under both temperatures the viscosity of the G6 polymer is much lower than for the control G1 polymer. At a temperature of 325° F. the time to double the viscosity was approximately 0.20 days for the control G1 polymer; however for the G6 polymer according to the present invention the time was 3.2 days. This is an increase in viscosity stability of almost 16 fold. At the lower temperature of 275° F. the G1 polymer viscosity was doubled within 1.6 days; however the G6 polymer at the same time had an increase of only approximately 0.1. At this lower temperature the viscosity of the G6 adhesive increased by only 15% after 4.25 days at which time the testing was stopped. At the lower temperature the G6 was dramatically more hot melt viscosity stable than the control G1 adhesive. In summary, the polymer containing G6 photoinitiator according to the present invention has significantly higher hot melt viscosity stability compared to the control photoinitiator G1 in the same polymer.

Adhesion Data

The acrylic polymers containing either G1 or G6 photoinitiator were combined with the tackifier Foral® 105 at a ratio of 100 parts polymer dry weight to 20 parts tackifier. The polymers with tackifier were coated onto the substrate, then UVC cured and then tested for shear and peel strength before and after UVC cure. The UVC cure exposure was calculated using a radiometer EIT Power Puck. The adhesive is either coated onto a release liner, exposed to UVC and then transferred to a backing substrate of polyethylene terephthalate (PET) or it is directly coated onto the PET film prior to exposure to the UVC. Strips 1" wide by 4" long were cut and applied to the substrates of interest. The shear strength was measured according to Pressure Sensitive Tape Counsel PSTC-7 or by ASTM D3654 using a 4.4 pounds per square inch (psi) load. The peel strength was measured by PSTC 101 or ASTM D3330. The results are shown in Table 1 below. The results show that the control G1 photoinitiator and the photoinitiator G6 according to the present invention produced similar shear and peel strength results both with and without crosslinking by UVC exposure.

TABLE 1

| PI in acrylate polymer | Tackifier (20:100) | 0 mJ/cm² UVC | | 50 mJ/cm² UVC | |
|---|---|---|---|---|---|
| | | Shear (4.4 psi-hr) | Peel (ozf/in) | Shear (hr) | Peel (ozf/in) |
| G-1 (control) | Foral ® 105 | 0.1 | 98 | >40 | 32 |
| G-6 (invention) | Foral ® 105 | 0.1 | 92 | >40 | 28 |

The adhesion properties of the acrylic PSA can be tailored by changing the monomers or monomer ratio in the acrylic polymer and PSA formulation. Table 2 below shows adhesion data for PSA's containing the photoinitiators G1, G6, or G10 on a PET backing substrate which was applied to a high density polyethylene substrate. Both G6 and G10 are in accordance with the present invention, while G1 is the control photoinitiator not in accordance with the present invention. The data again shows that the photoinitiators all produce about the same shear and peel strength on a high density polyethylene substrate. The photoinitiators G6 and G10, in accordance with the present invention, however are far superior in terms of hot melt viscosity stability compared to G1. Both G6 and G10 had much longer times to double the viscosity at either 275° F. or 325° F. compared to G1. In addition, the G6 photoinitiator was more reactive than G1 and G10 since it required a lower UVC dosage to cure.

TABLE 2

| Photoinitiator | Shear (4.4 psi-hr) | HDPE peel (ozf/in) | UVC dosage mJ/cm² | Viscosity (time in days to double) | |
|---|---|---|---|---|---|
| | | | | 275° F. | 325° F. |
| G1 (control) | 30 | 38 | 40 | 1.6 | 0.2 |
| G6 | 32 | 39 | 30 | >7 | 3.2 |
| G10 | 32 | 36 | 40 | na | 2.9 |

In summary, photoinitiators prepared according to the present invention are able to substitute in directly for existing photoinitiators and exhibit better characteristics. Specifically, the photoinitiators according to the present invention have much higher hot melt viscosity stability compared to previous photoinitiators, on the order of 10 fold greater or more. In addition, the present initiators have a slightly better UVC reactivity in many cases compared to the previously available photoinitiators. The present photoinitiators are expected to find wide ranging use in all types of HMPSA applications. Preferably the photoinitiators are utilized with acrylic polymers to form HMPSAs which can in turn be used to form a variety of articles as known to those of skill in the art.

The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

We claim:

1. A photoinitiator having a structure as defined in formula I below:

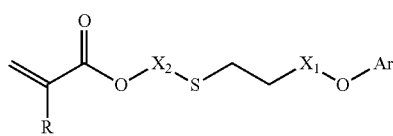

Formula I wherein:

Ar is selected from the group consisting of:

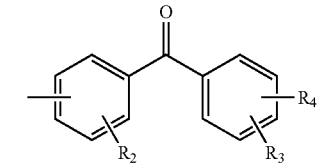

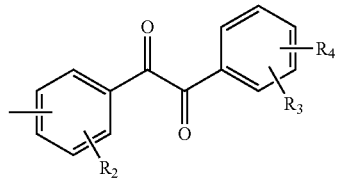

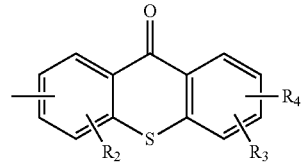

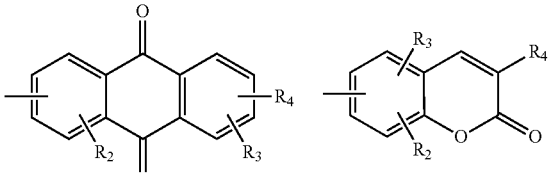

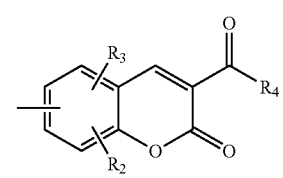

wherein:

R$_2$, R$_3$ and R$_4$ are independently: a linear alkyl group; a branched alkyl group; a cycloalkyl group; an alkylenoxy group; an alkenyl group; an aryl group; or an alkyl group containing a heteroatom; a carbonyl group; H; F; Cl; Br; I; OR; NR$_2$; or SR wherein R in OR, NR$_2$, or SR is one of an alkyl, an aryl, or a heteroaryl group;

X$_1$ is optional, if present it is one of: CH$_2$; a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; or a cycloalkyl group containing at least one of heteroatoms, a carbonyl, an ester, a carbonate, and mixtures thereof at any position;

X$_2$ is one of: a linear alkyl group; a branched alkyl group; a cycloalkyl group; a linear alkyl group containing at least one of heteroatoms, a carbonyl, an ester, a carbonate, and mixtures thereof at any position; a branched alkyl group containing at least one of heteroatoms, a carbonyl, an ester, a carbonate, and mixtures thereof at any position; or a cycloalkyl group containing at least one of heteroatoms, a carbonyl, an ester, a carbonate, and mixtures thereof at any position; and R is H or CH$_3$.

2. The photoinitiator as recited in claim 1, wherein the photoinitiator is selected from the group consisting of:

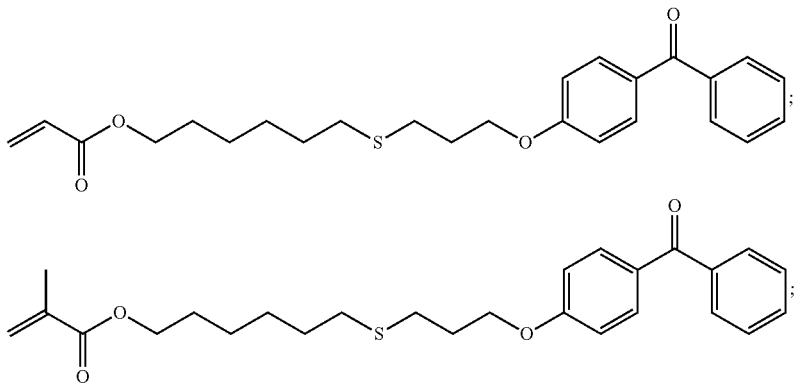

and mixtures thereof.

3. An ultra violet light curable polymer comprising:
an acrylic polymer that is a reaction product of a plurality of one or more acrylic monomers and one or more photoinitiators according to claim 1, wherein said acrylic polymer is crosslinkable through said photoinitiator groups upon exposure to ultra violet light.

4. The ultra violet light curable polymer according to claim 3 wherein the photoinitiator is present in an amount of from 0.1 to 10 mole percent based on the total number of moles of acrylate monomers used for polymerization to obtain the acrylic polymer.

5. The ultra violet light curable polymer according to claim 3 wherein the photoinitiator is selected from the group consisting of:

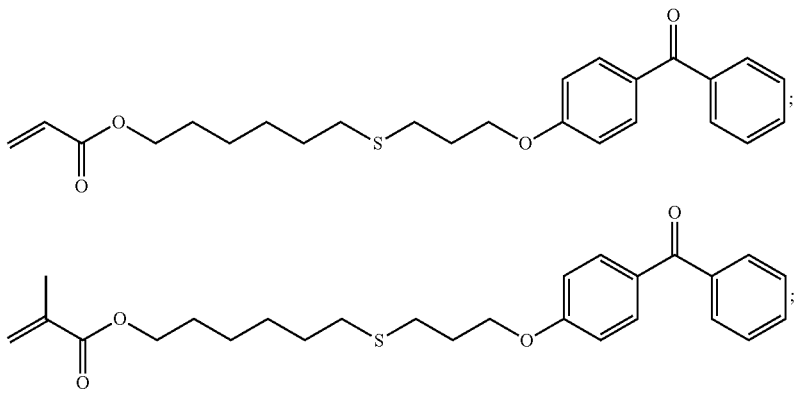

and mixtures thereof.

6. The ultra violet light curable polymer according to claim 3 wherein the acrylic monomers are selected from the group consisting of: acrylic acid, methacrylates, methyl methacrylates, ethyl acrylates, 2-chloroethyl vinyl ethers, 2 ethylhexyl acrylate, acetoacetoxyethyl methacrylate (AAEM), hydroxyethyl methacrylate, butyl acrylate, butyl methacrylate, trimethylolpropane triacrylate (TMPTA), and mixtures thereof.

7. A hot melt pressure sensitive adhesive that is ultra violet light curable and comprises:
  an acrylic polymer that is a reaction product of a plurality of one or more acrylic monomers and one or more photoinitiators according to claim 1, wherein said acrylic polymer is crosslinkable through said photoinitiator groups upon exposure to ultra violet light, and optionally a tackifier.

8. The hot melt pressure sensitive adhesive that is ultra violet light curable according to claim 7 wherein at least one tackifier is present and said at least one tackifier comprises a rosin ester, a terpene phenol, an ester of a hydrogenated rosin, a synthetic hydrocarbon, and mixtures thereof.

* * * * *